(12) United States Patent
Dawkins et al.

(10) Patent No.: US 10,207,970 B2
(45) Date of Patent: *Feb. 19, 2019

(54) METHODS FOR RECOVERING CHLORINATED HYDROCARBONS

(71) Applicant: OCCIDENTAL CHEMICAL CORPORATION, Dallas, TX (US)

(72) Inventors: John Lee Dawkins, Derby, KS (US); Darrell G Hollis, Conway Springs, KS (US); Rodney L Klausmeyer, Wichita, KS (US); Keith S Kramer, Andover, KS (US); Michael A Garmon, Manvel, TX (US)

(73) Assignee: Occidental Chemical Corporation, Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/449,017

(22) Filed: Mar. 3, 2017

(65) Prior Publication Data
US 2017/0174590 A1 Jun. 22, 2017

Related U.S. Application Data

(63) Continuation of application No. 14/767,417, filed as application No. PCT/US2014/016026 on Feb. 12, (Continued)

(51) Int. Cl.
*C07C 17/42* (2006.01)
*C07C 17/395* (2006.01)
(Continued)

(52) U.S. Cl.
CPC ............ *C07C 17/386* (2013.01); *B01D 3/009* (2013.01); *B01D 3/10* (2013.01); *B01D 3/34* (2013.01);
(Continued)

(58) Field of Classification Search
CPC ...... C07C 17/38; C07C 17/383; C07C 17/386
See application file for complete search history.

(56) References Cited

U.S. PATENT DOCUMENTS

| 4,307,261 A | 12/1981 | Beard, Jr. et al. |
| 6,313,360 B1 | 11/2001 | Wilson et al. |
| 8,115,038 B2 | 2/2012 | Wilson et al. |

FOREIGN PATENT DOCUMENTS

| CN | 100 427 442 C | 10/2008 |
| WO | 97/07083 A1 | 2/1997 |

(Continued)

OTHER PUBLICATIONS

International Search Report for International Application No. PCT/US2014/016026 dated May 28, 2014.

*Primary Examiner* — Medhanit W Bahta
(74) *Attorney, Agent, or Firm* — Renner, Kenner; Arthur M. Reginelli (57) ABSTRACT

Processes for isolating 1,1,1,2,3-pentachloropropane from a crude product stream containing the 1,1,1,2,3-pentachloropropane and ferric chloride. The processes may include deep distillation of the crude, treatment of the crude with a reagent that deactivates the ferric chloride followed by distillation on the deactivated crude stream, aqueous washing of the crude product stream to remove ferric chloride followed by distillation on the deactivated crude stream. Other embodiments simultaneously prepare 1,1,2,3-tetrachloroprene and 1,1,1,2,3-pentachloroprane.

16 Claims, 5 Drawing Sheets

Related U.S. Application Data 2014, now Pat. No. 9,598,337, which is a continuation of application No. 13/831,064, filed on Mar. 14, 2013, now Pat. No. 9,067,858.

(60) Provisional application No. 61/763,583, filed on Feb. 12, 2013.

(51) Int. Cl.

| | |
|---|---|
| *C07C 17/383* | (2006.01) |
| *C07C 17/386* | (2006.01) |
| *C07C 19/01* | (2006.01) |
| *B01J 27/128* | (2006.01) |
| *C07C 17/25* | (2006.01) |
| *C07C 17/38* | (2006.01) |
| *B01D 3/10* | (2006.01) |
| *B01D 3/34* | (2006.01) |
| *B01D 3/00* | (2006.01) |
| *B01D 11/04* | (2006.01) |
| *C07C 17/06* | (2006.01) |
| *C07C 17/278* | (2006.01) |

(52) U.S. Cl.
CPC .............. *B01D 11/04* (2013.01); *B01J 27/128* (2013.01); *C07C 17/25* (2013.01); *C07C 17/38* (2013.01); *C07C 17/383* (2013.01); *C07C 17/395* (2013.01); *C07C 17/42* (2013.01); *C07C 19/01* (2013.01); *C07C 17/06* (2013.01); *C07C 17/278* (2013.01); *Y02P 20/127* (2015.11)

(56) References Cited

FOREIGN PATENT DOCUMENTS

| | | |
|---|---|---|
| WO | 00/35839 A1 | 6/2000 |
| WO | 00/68172 A1 | 11/2000 |

METHODS FOR RECOVERING CHLORINATED HYDROCARBONS

This application is a continuation of U.S. Non-Provisional application Ser. No. 14/767,417 filed Aug. 12, 2015, which is a National-Stage application of International application PCT/US2014/016026 filed Feb. 12, 2014, which is a continuation application of U.S. Ser. No. 13/831,064 filed Mar. 14, 2013, which claims the benefit of U.S. Provisional Application Ser. No. 61/763,583 filed on Feb. 12, 2013, which are incorporated herein by reference.

FIELD OF THE INVENTION

Embodiments of the present invention are directed toward methods for recovering chlorinated hydrocarbons, especially chloropropanes, from crude reactant streams containing the chlorinated hydrocarbons.

BACKGROUND OF THE INVENTION

U.S. Pat. No. 8,115,038 discloses a method for producing 1,1,1,2,3-pentachloropropane from 1,1,1,3-tetrachloropropane by heating 1,1,1,3-tetrachloropropane in the presence of ferric chloride and chlorine. The product of this direct chlorination is a mixture that is referred to as crude 1,1,1,2,3-pentachloropropane liquid. This crude may include, in addition to the 1,1,1,2,3-pentachloropropane, ferric chloride, 1,1,1,3-tetrachloropropane, 1,1,3-trichloropropene, and 1,1,2,3-tetrachloropropene, as well as hexachloropropane.

U.S. Pat. No. 8,115,038 discloses that the 1,1,1,2,3-pentachloropropane can be directly treated within a reactive distillation column to produce 1,1,2,3-tetrachloropropene. In the alternative, this patent discloses that the 1,1,1,2,3-pentachloropropane can be further purified. While conventional techniques for purification may be evident to the skilled person, commercially efficient techniques for separating the 1,1,1,2,3-pentachloropropane from the crude 1,1,1,2,3-pentachloropropane liquid would be desirable.

SUMMARY OF THE INVENTION

One or more embodiments of the present invention provides a process for isolating 1,1,1,2,3-pentachloropropane from a crude product stream containing the 1,1,1,2,3-pentachloropropane, the process comprising providing a crude product stream containing 1,1,1,2,3-pentachloropropane, where the crude product stream includes ferric chloride, subjecting the crude product stream to distillation at a pressure of less than 0.040 atmospheres to thereby form a stream including 1,1,1,2,3-pentachloropropane that is substantially free of ferric chloride, and further processing the stream to isolate 1,1,1,2,3-pentachloropropane.

Still other embodiments of the present invention provide a process for isolating 1,1,1,2,3-pentachloropropane from a crude product stream containing the 1,1,1,2,3-pentachloropropane, the process comprising providing a crude product stream containing 1,1,1,2,3-pentachloropropane, where the crude product stream further includes ferric chloride, adding a reagent to the crude product stream to deactivate the ferric chloride, after said step of adding a reagent, subjecting the crude product stream to distillation to thereby form a 1,1,1,2,3-pentachloropropane stream that is substantially free of ferric chloride, and further processing the 1,1,1,2,3-pentachloropropane stream to isolate the 1,1,1,2,3-pentachloropropane.

Still other embodiments of the present invention provide a process for isolating 1,1,1,2,3-pentachloropropane from a crude product stream containing the 1,1,1,2,3-pentachloropropane, the process comprising providing a crude product stream containing 1,1,1,2,3-pentachloropropane, where the crude product stream includes ferric chloride, combining the crude product stream with water to form a mixture, allowing the mixture to phase separate and thereby form an aqueous phase and an organic phase, where the aqueous phase includes ferric chloride and the organic phase is substantially free of ferric chloride, separating the aqueous phase from the organic phase, and further processing the organic phase to isolate 1,1,1,2,3-pentachloropropane.

Still other embodiments of the present invention provide a process for simultaneously producing purified streams of 1,1,2,3-tetrachloropropene and 1,1,1,2,3-pentachloropropane, the process comprising providing a crude product stream containing 1,1,1,2,3-pentachloropropane, where the crude product stream includes ferric chloride and subjecting the crude product stream to distillation at a pressure sufficient to convert a portion of the 1,1,1,2,3-pentachloropropane within the crude to 1,1,2,3-tetrachloropropene while simultaneously forming a volatiles fraction including the 1,1,1,2,3-pentachloropropane and 1,1,2,3-tetrachloropropene, where the volatiles fraction is substantially free of ferric chloride.

Still other embodiments of the present invention provide a process for simultaneously producing purified streams of 1,1,2,3-tetrachloropropene and 1,1,1,2,3-pentachloropropane, the process comprising providing a crude product stream containing 1,1,1,2,3-pentachloropropane, where the crude product stream includes ferric chloride, subjecting the crude product stream to reactive distillation within a distillation column under conditions sufficient to form a gradient within the column, where the gradient includes a maximum concentration of 1,1,1,2,3-pentachloropropane at the bottom of the gradient and maximum of 1,1,2,3-tetrachloropropene at the top of the gradient, and removing the 1,1,1,2,3-pentachloropropane from the distillation column at a location within the gradient proximate to the maximum concentration of 1,1,1,2,3-pentachloropane within the gradient.

DETAILED DESCRIPTION OF ILLUSTRATIVE EMBODIMENTS

Embodiments of the present invention provide techniques for separating 1,1,1,2,3-pentachloropropane from crude 1,1, 1,2,3-pentachloropropane streams. In one or more embodiments, the crude 1,1,1,2,3-pentachloropropane stream may contain ferric chloride or other catalysts that promote the dehydrochlorination of the 1,1,1,2,3-pentachloropropane. Thus, embodiments of the present invention advantageously provide for the isolation of 1,1,1,2,3-pentachloropropane without substantially converting appreciable amounts of 1,1,1,2,3-pentachloropropane to 1,1,2,3-tetrachloropropene. In other embodiments, the techniques of the present invention provide a process whereby both purified 1,1,1,2,3-pentachloropropane and 1,1,2,3-tetrachloropropene can be produced at desired levels.

Process for Producing 1,1,1,2,3-Pentachloropropane Crude

In one or more embodiments, a crude product stream containing 1,1,1,2,3-pentachloropropane may be produced by using known methods. In this regard, U.S. Pat. No. 8,115,038 is incorporated by reference. In one or more embodiments, the crude product stream containing 1,1,1,2,3-pentachloropropane may be produced within a single reactor vessel where 1,1,1,3-tetrachloropropane is converted to 1,1,1,2,3-pentachloropropane in the presence of chlorine and ferric chloride.

Characteristics of 1,1,1,2,3-Pentachloropropane Crude

In one or more embodiments, the crude product stream containing 1,1,1,2,3-pentachloropropane, which may also be referred to as crude 1,1,1,2,3-pentachloropropane, includes at least 50 wt. %, in other embodiments at least 60 wt. %, and in other embodiments at least 70 wt. % 1,1,1,2,3-pentachloropropane. In particular embodiments, the crude product stream may include from about 50 to about 90 or in other embodiments from about 70 to about 80 wt. % 1,1,1,2,3-pentachloropropane.

In one or more embodiments, the crude product stream also includes ferric chloride. In one or more embodiments, the crude product stream includes at least 10 ppm, in other embodiments at least 25 ppm, in other embodiments at least 50 ppm, in other embodiments at least 80 ppm, and in other embodiments at least 100 ppm by weight ferric chloride. In particular embodiments, the crude product stream includes from about 50 to about 500 ppm or in other embodiments from about 70 to about 200 ppm by weight ferric chloride.

In one or more embodiments, the crude product stream also includes carbon tetrachloride. In one or more embodiments, the crude product stream includes at most 50 wt. %, in other embodiments at most 30 wt. %, and in other embodiments at most 20 wt. % carbon tetrachloride. In particular embodiments, the crude product stream includes from about 5 to about 30 wt. % or in other embodiments from about 10 to about 20 wt. % carbon tetrachloride.

In one or more embodiments, the crude product stream also includes 1,1,1,3-tetrachloropropane. In one or more embodiments, the crude product stream includes at most 20 wt. %, in other embodiments at most 10 wt. %, and in other embodiments at most 5 wt. % 1,1,1,3-tetrachloropropane. In particular embodiments, the crude product stream includes from about 0 to about 5 wt. % or in other embodiments from about 0 to about 2.5 wt. % 1,1,1,3-tetrachloropropane.

First Embodiment—Low-Pressure Distillation

In a first embodiment, the process for isolating the 1,1,1,2,3-pentachloropropane from a crude product stream includes the use of low-pressure distillation, which may also be referred to as deep distillation. By employing low-pressure distillation, the 1,1,1,2,3-pentachloropropane can be separated by distillation from iron chlorides within the crude product stream without elevating the temperature of the crude to temperatures that can cause conversion, or appreciable conversion, of the 1,1,1,2,3-pentachloropropane to 1,1,2,3-tetrachloropropene by dehydrochlorination. As a result, the 1,1,1,2,3-pentachloropropane can be subsequently separated from other constituents within the crude by using commercially efficient separation techniques, such as distillation at higher temperatures and/or pressures, without converting substantial amounts of 1,1,1,2,3-pentachloropropane to 1,1,2,3-tetrachloropropene by dehydrochlorination.

In one or more embodiments, the low-pressure distillation of the crude product stream may take place at less than 0.040 atmospheres, in other embodiments less than 0.027 atmospheres, in other embodiments less than 0.020 atmospheres, and in other embodiments less than 0.015 atmospheres. In particular embodiments, the low-pressure distillation may take place at from about 0.001 to about 0.040 atmospheres or in other embodiments from about 0.003 to about 0.027 atmospheres.

In one or more embodiments, low-pressure or deep distillation of the crude product stream takes place at a temperature of less than 120° C., in other embodiments less than 100° C., in other embodiments less than 75° C., and in other embodiments less than 50° C. In particular embodiments, the low-pressure distillation takes place at a temperature from about 30 to about 120° C. or in other embodiments from about 40 to about 100° C.

Figure 1:
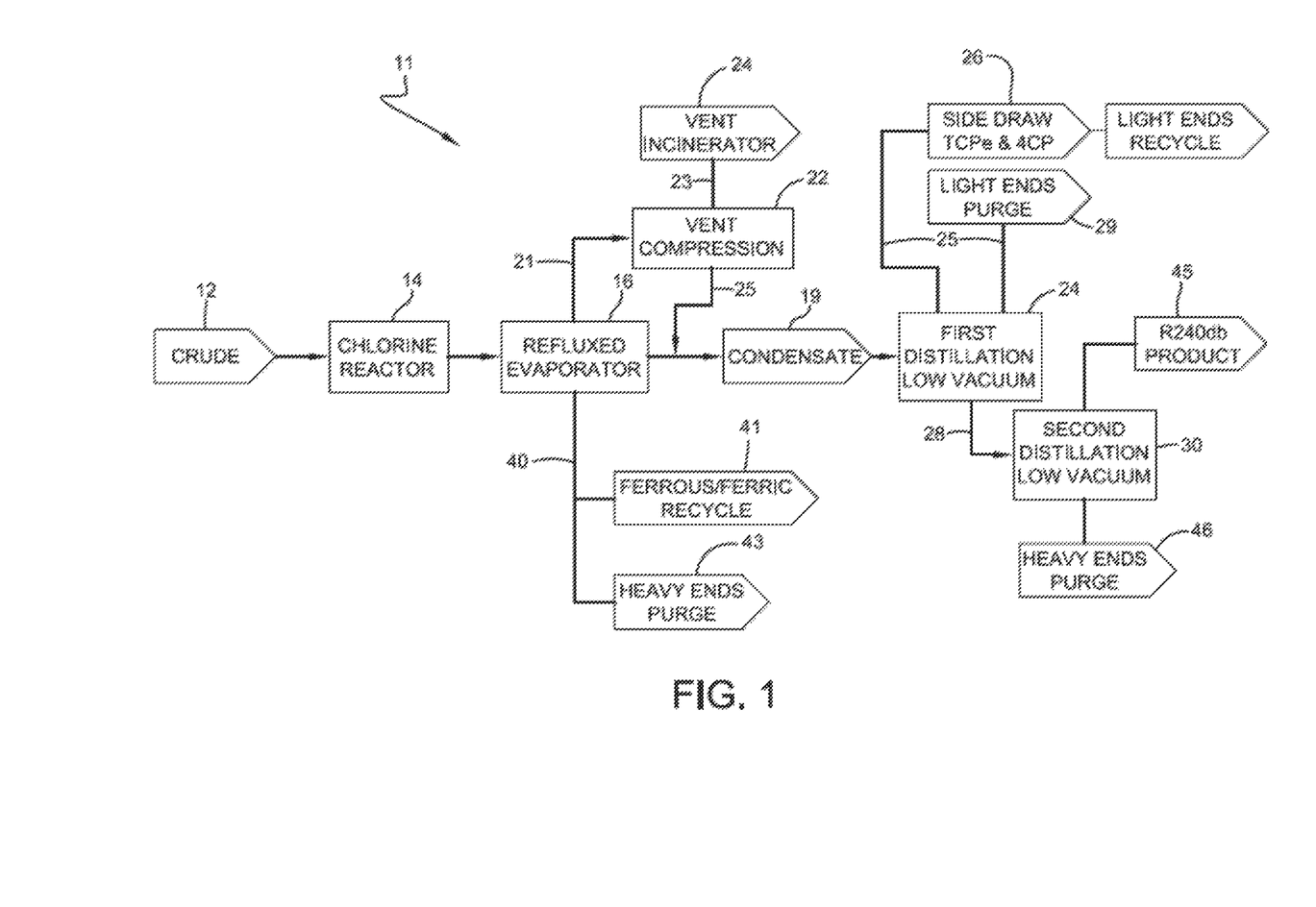
FIG. 1 is a schematic representation of a process for isolating 1,1,1,2,3-pentachloropropane according to one or more embodiments of the invention where deep vacuum distillation is employed.

An exemplary process for isolating 1,1,1,2,3-pentachloropropane is shown in FIG. 1. The process 11 includes providing a crude product stream 12, which includes 1,1,1,2,3-pentachloropropane, which may also be referred to as HCC-240db or 240db. As discussed above, crude 12 includes ferric chloride. In one or more embodiments, crude 12 is optionally transferred to an optional residence tank 14, which may also be referred to as optional chlorine reactor 14, wherein residual chlorine within crude 12 is provided sufficient residence time to convert to chlorinated organic products.

Crude 12 is then distilled under low-pressure vacuum within, for example, a reflux evaporator 16 to produce condensate fraction 19. As suggested above, evaporator 16 may be operated at pressures of less than 0.040 atmospheres, in other embodiments less than 0.027 atmospheres, and in other embodiments less than 0.020 atmospheres. In these or other embodiments, evaporator 16 may be operated at temperatures of less than 100° C., in other embodiments less than 75° C., and in other embodiments less than 50° C.

In one or more embodiments, a non-condensed fraction 21 is routed to a compression unit 22 where the non-condensed fraction 21 is partially condensed within vent compression and recovery unit 22. Waste stream 23 from vent compression and recovery unit 22 may be subsequently treated in vent incinerator 24, while condensate 25 from compression and recovery unit 22 can be merged with condensate 19.

The bottom fraction 40 of evaporator 16, which is believed to include iron chlorides, is routed to a heavy ends purge 43. In one or more embodiments, a portion of bottom fraction 40, especially the fraction believed to contain iron chlorides, can be recycled back to one or more processes where ferric chloride is employed. For example, iron chlorides 41 can be recycled back to a reactor in which crude 12 is produced.

In one or more embodiments, condensate 19, which includes the desired 1,1,1,2,3-pentachloropropane, is further fractionated to isolate 1,1,1,2,3-pentachloropropane from other compounds that were collected with condensate 19 from evaporator 16. For example, condensate 19 can be routed to a distillation column 24 for further fractionating. Advantageously, condensate 19 is substantially free of ferric chloride or other catalytic materials that could promote dehydrochlorination of the 1,1,1,2,3-pentachloropropane, and therefore efficient fractionating of condensate 19 may be performed. The term "substantially free of ferric chloride" refers to that amount of ferric chloride or less that will not have an appreciable impact on the ability to further fraction the 1,1,1,2,3-pentachloropropane from other constituents within condensate 19. In particular embodiments, condensate 19 includes less than 100 ppm, in other embodiments less than 10 ppm, in other embodiments less than 5 ppm, and in other embodiments less than 1 ppm by weight ferric chloride.

In one or more embodiments, the fractionating of condensate 19 can take place using one or more columns. The various fractions within condensate 19 can be separated as overhead fractions and/or side-draw fractions from the one or more columns.

For example, and as shown in FIG. 1, multiple distillation columns are employed. First column 24 can be operated at or under pressures greater than 0.040 atmospheres, in other embodiments greater than 0.050 atmospheres, in other embodiments greater than 0.070 atmospheres, in other embodiments greater than 0.095 atmospheres, and in other embodiments greater than 0.105 atmospheres. In these or other embodiments, first column 24 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, distillation column 24 is operated at from about 0.050 to about 0.250 atmospheres or in other embodiments from about 0.095 to about 0.130 atmospheres.

As shown in FIG. 1, the volatiles fraction 25 from distillation column 24 may include a first fraction 26, which may also be referred to as side draw 26, that includes 1,1,1,3-tetrachloropropane and 1,1,3-trichloropropene, and a second fraction 29 that includes light ends, which include those compounds that are more volatile than the 1,1,1,3-tetrachloropropane and 1,1,3-trichloropropene. In one or more embodiments, first fraction 26 may be recycled back to one or more processes. For example, first fraction 26 can be recycled back to a reactor in which crude 12 is produced.

The bottoms fraction 28 from distillation column 24, which contains the desired 1,1,1,2,3-pentachloropropane product, may be further fractioned to isolate the 1,1,1,2,3-pentachloropropane from other high boiling compounds within bottom fraction 28. For example, bottoms fraction 28 may be routed to a second distillation column 30. In one or more embodiments, second distillation column 30 is operated at pressures greater than 0.050 atmospheres, in other embodiments greater than 0.070 atmospheres, in other embodiments greater than 0.095 atmospheres, and in other embodiments greater than 0.105 atmospheres. In these or other embodiments, second distillation column 30 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, second distillation column 30 is operated at from about 0.050 to about 0.250 atmospheres or in other embodiments from about 0.095 to about 0.130 atmospheres. The desired 1,1,1,2,3-pentachloropropane product 45 is collected as a separate stream from heavy ends 46 leaving second distillation column 30.

Second Embodiment—Use of Deactivating Agent

In a second embodiment, which may be employed in conjunction with the first embodiment or with one or more aspects of the first embodiment, one or more reagents (also referred to as inhibitors) are combined with the crude 1,1,1,2,3-pentachloropropane stream in order to deactivate the ferric chloride and optionally other catalytic constituents within the crude that could promote dehydrochlorination of the 1,1,1,2,3-pentachloropropane. In one or more embodiments, the crude 1,1,1,2,3-pentachloropropane stream that is treated according to these embodiments can be subjected to distillation techniques in order to separate the 1,1,1,2,3-pentachloropropane, as well as other generally similar chlorinated organics, from the ferric chloride or other iron compounds, and further fractionated to obtain a purified 1,1,1,2,3-pentachloropropane stream. This may be accomplished by subjecting the treated stream to deep distillation (consistent with the embodiments set forth above), and then subjecting the stream to more commercially efficient fractionating processes such as distillation at pressures nearer atmospheric pressure. In other embodiments, the crude treated according to these embodiments can be directly subjected to commercially efficient techniques, such as distillation at elevated temperatures, without first undergoing deep distillation, in order to obtain a purified 1,1,1,2,3-pentachloropropane stream without converting substantial amounts of 1,1,1,2,3-pentachloropropane to 1,1,2,3-tetrachloropropene.

In one or more embodiments, the crude product stream, which includes the 1,1,1,2,3-pentachloropropane, is treated with an inhibitor that inhibits the catalytic activity of the ferric chloride. In one or more embodiments, the inhibitor binds with the ferric chloride and thereby inactivates its ability to catalyze the dehydrochlorination of the 1,1,1,2,3-pentachloropropane. In other embodiments, the inhibitor reduces the ferric chloride to compounds such as ferrous chloride, which does not catalyze the dehydrochlorination of the 1,1,1,2,3-pentachloropropane.

In one or more embodiments, the inhibitor is a Lewis base. In particular embodiments, the inhibitor is a phosphorus-containing Lewis base. In particular embodiments, the Lewis base is tributylphosphate. In one or more embodiments, the amount of the Lewis base (e.g., tributylphosphate) added to the crude product stream is at least 0.5 moles, in other embodiments at least 0.7 mole, in other embodiments at least 1.0 mole, and in other embodiments at least 1.3 moles of Lewis base per mole of ferric chloride within the crude product stream. In these or other embodiments, the amount of Lewis base (e.g., tributylphosphate) added to the crude product stream is at most 25 moles, in other embodiments at most 10 moles, in other embodiments at most 5 moles, and in other embodiments at most 2 moles of Lewis base per mole of ferric chloride within the crude product stream. In particular embodiments, the amount of Lewis base added to the crude product stream is from about 0.5 to about 25 moles or in other embodiments from about 0.7 to about 5 moles of Lewis base per mole of ferric chloride within the crude product stream. In particular embodiments, the use of Lewis base has proven unexpectedly useful in that any reactions products formed within the crude stream treated with the Lewis base have not proven to be deleterious to the crude or further processing of the crude. For example, it has unexpectedly been observed that the crude remains relatively clear with no appreciable solids, which solids could suggest side reactions or polymerization of constituents that could be problematic for future processing or deleterious to equipment.

In other embodiments, the reagent added to the crude product stream is a hydrocarbon oil. In this regard, U.S. Pat. No. 4,307,261 is incorporated herein by reference. It is believed that the hydrocarbon oil will react or interact with the ferric chloride to reduce the ferric chloride to a ferrous state and thus form a solid precipitate of iron compounds combined with a small amount of carbonaceous material. In one or more embodiments, the hydrocarbon oil employed has a boiling temperature that is higher than the 1,1,1,2,3-pentachloropropane, and as a result, the 1,1,1,2,3-pentachloropropane can be easily separated from the hydrocarbon oil.

Examples of hydrocarbon oils that can be employed in practicing these aspects of the present invention include hydrocarbon oils or partially chlorinated hydrocarbon oils. In one or more embodiments, the oils are hydrocarbons that include at least six carbon atoms, e.g. 6 to 40 or more carbon atoms. Oil compositions containing an average of at least 12 and up to 40 carbon atoms per molecule are employed in particular embodiments. Specific examples include, but are not limited to, alkanes, alkenes, alkyl benzenes, alkyl naphthalenes, cycloalkanes, cycloalkenes or the like, or mixtures of two or more of these hydrocarbons or kinds of hydrocarbons. In particular embodiments, especially when alkylated aromatics are used as the reducing oil, oil compositions including a major or at least a substantial proportion of aromatic compounds having at least one aliphatic side chain containing six or more carbon atoms are used, e.g., n-hexyl benzene, nonylnaphthalene, etc. Cycloalkenes, such as cyclohexene or cyclooctene, may also be used. Partially chlorinated derivatives of the hydrocarbons listed above and mixtures of the foregoing, especially the mono, di-, tri- or tetrachlorinated derivatives, are similarly useful.

In one or more embodiments, the amount of hydrocarbon oil added to the crude product stream may be explained with reference to the amount of chlorinated organics (e.g. 1,1,1,2,3-pentachloropropane) within the crude product stream. In one or more embodiments, the amount of oil added to the crude product stream is at least 1 mole, in other embodiments at least 2 moles, and in other embodiments at least 10 moles of oil per mole of ferric chloride within the crude product stream. In these or other embodiments, the amount of oil added to the crude product stream is at most 100 moles, in other embodiments at most 50 moles, and in other embodiments at most 20 moles oil per mole of ferric chloride within the crude product stream. In particular embodiments, the amount of oil added to the crude product stream is from about 1 to about 100 or in other embodiments from about 2 to about 50 moles of oil per mole of ferric chloride within the crude product stream.

Figure 2:
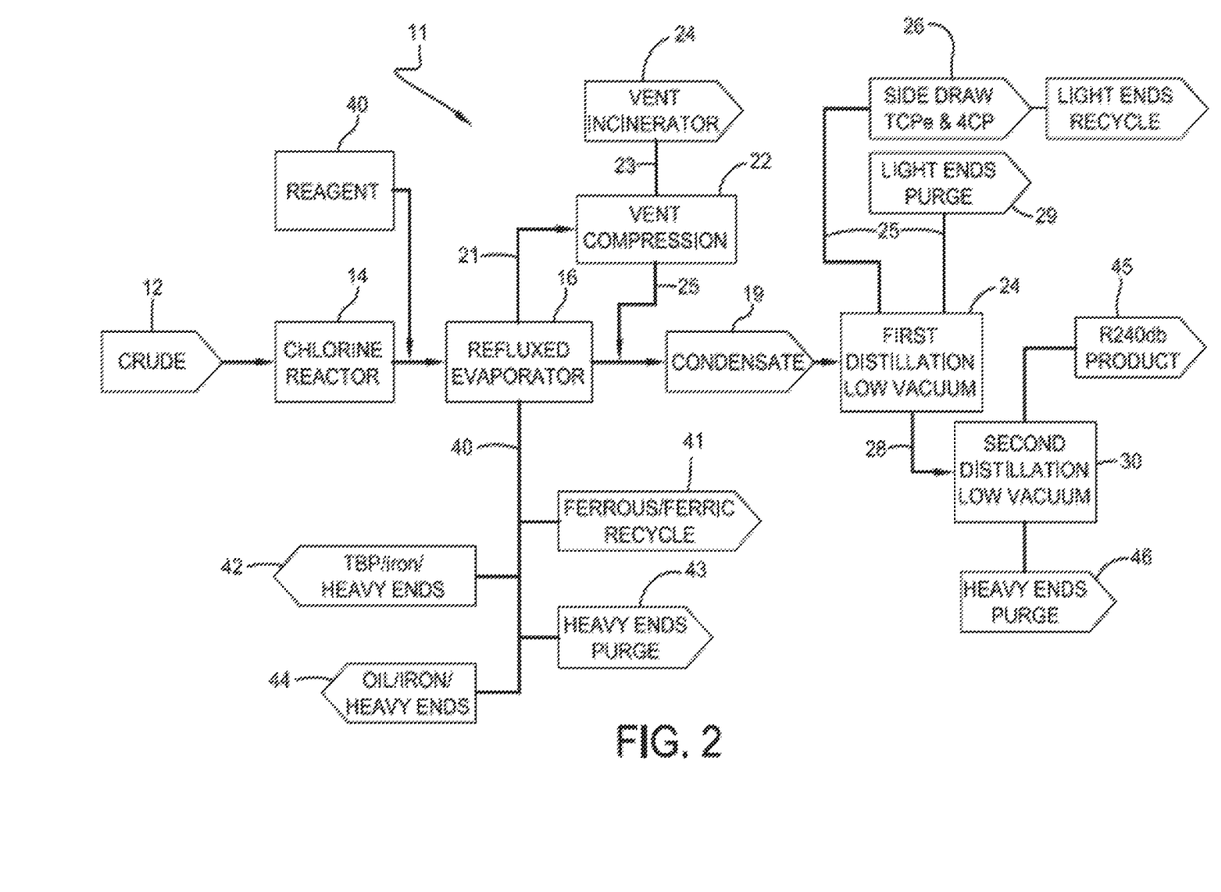
FIG. 2 is a schematic representation of a process for isolating 1,1,1,2,3-pentachloroproprane according to one or more embodiments of the invention where an inhibitor is employed optionally together with deep vacuum distillation.

Reference can be made to FIG. 2 to further explain exemplary aspects of these embodiments. As shown in FIG. 2, reagent 40 can be added to the crude product stream 12 in order to deactivate the ferric chloride. This may optionally take place once crude product stream 12 exits optional chlorine reactor 14.

In particular embodiments, product stream containing reagent 40 (which is believed to include deactivated ferric chloride or the reaction products or complex of the inhibitor and ferric chloride) can be subjected to deep distillation separation techniques as describe above. For example, the product stream treated with reagent 40 can be routed to evaporator 16 where it is subjected to deep distillation techniques. As noted above, this may include low-pressure distillation at less than 0.040 atmospheres, in other embodiments less than 0.027 atmospheres, in other embodiments less than 0.020 atmospheres, and in other embodiments less than 0.015 atmospheres. In particular embodiments, the low-pressure distillation may take place at from about 0.001 to about 0.040 atmospheres or in other embodiments from about 0.003 to about 0.027 atmospheres.

In other embodiments, since the ferric chloride is believed to be deactivated, crude product stream 12 can be treated in an evaporator or distillation column 16 at higher temperatures or pressures. For example, evaporator/distillation column 16 may be operated at pressures greater than 0.040 atmospheres, in other embodiments greater than 0.050 atmospheres, in other embodiments greater than 0.070 atmospheres, in other embodiments greater than 0.095 atmospheres, and in other embodiments greater than 0.105 atmospheres. In these or other embodiments, evaporator/distillation column 16 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, evaporator/distillation column 16 is operated at from about 0.050 to about 0.250 atmospheres or in other embodiments from about 0.095 to about 0.130 atmospheres.

In any event, condensate 19 may advantageously be substantially free of ferric chloride or other catalytic materials that could promote dehydrochlorination of the 1,1,1,2,3-pentachloropropane, and therefore efficient fractionating of condensate 19 may be performed. The term "substantially free of ferric chloride" refers to that amount of ferric chloride or less that will not have an appreciable impact on the ability to further fraction the 1,1,1,2,3-pentachloropropane from other constituents within condensate 19. In particular embodiments, condensate 19 includes less than 100 ppm, in other embodiments less than 10 ppm, in other embodiments less than 5 ppm, and in other embodiments less than 1 ppm by weight ferric chloride.

Condensate 19 may then be treated in a similar fashion as described above, while bottom fraction 40, which includes various species deriving from reactions or interactions between ferric chloride tributylphosphate and/or hydrocarbon oil is desirably removed from the process as waste. In one or more embodiments, condensate 19, which contains the desired 1,1,1,2,3-pentachloropropane product, may be further fractioned to isolate the 1,1,1,2,3-pentachloropropane from other high boiling compounds. For example, condensate 19 may be routed to a second distillation column 30, as described with respect to the first embodiment.

Third Embodiment-Aqueous Washing

In a third embodiment, the process for isolating the 1,1,1,2,3-pentachloropropane from a crude product stream includes the use of aqueous washing techniques to remove iron and/or iron chlorides from the crude. By removing the iron chlorides from the crude, as well as other catalytic materials that may be water soluble, the 1,1,1,2,3-pentachloropropane can be subsequently separated from other constituents within the crude without converting substantial amounts of 1,1,1,2,3-pentachloropropane to 1,1,2,3-tetrachloropropene by dehydrochlorination.

In one or more embodiments, this aqueous washing technique includes combining the crude with water and subsequently allowing the mixture to phase separate into an aqueous phase and an organic phase. In particular embodiments, once the water is combined with the crude product stream, the mixture may be agitated or intimately mixed so as to increase, through surface area, the boundary between the aqueous and organic phases. In one or more embodiments, mixing may be achieved by using an in-line mixer. Once the mixture is allowed to phase separate, the aqueous layer is separated from the organic layer and removed from the process (e.g., it is removed as aqueous waste). For example, the organic layer can be decanted by removing, such as pumping, the organic layer from the top of the separated mixture. The organic material can then be dried and the 1,1,1,2,3-pentachloropropane can be isolated using techniques such as those described above with respect to the previous embodiments.

Figure 3:
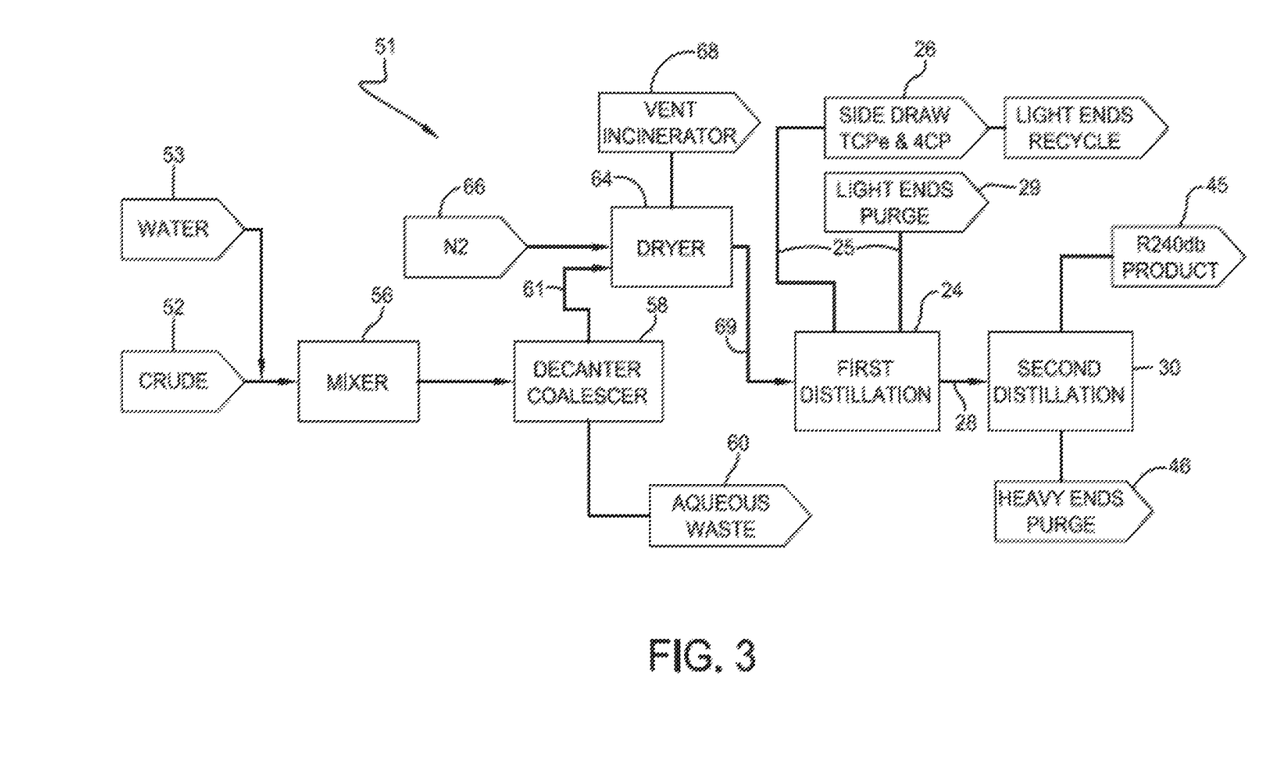
FIG. 3 is a schematic representation of a process for isolating 1,1,1,2,3-pentachloropropane according to one or more embodiments of the invention where aqueous washing is employed.

An exemplary process according to this embodiment is shown in FIG. 3. Process 51 includes providing a crude 1,1,1,2,3-pentachloropropane stream 52 and water stream 53, and combining and mixing crude 52 and water 53 within mixer 56. In one or more embodiments, the weight ratio of water to ferric chloride within the mixture may be at least 800:1, in other embodiments at least 1000:1, and in other embodiments at least 1200:1. In these or other embodiments, the weight ratio of water to ferric chloride within the mixture may be from about 800:1 to about 5000:1, in other embodiments from about 1000:1 to about 4000:1, and in other embodiments from about 1200:1 to about 3000:1.

The aqueous and organic phases of the mixture are separated by using, for example, a decanter/coalescer 58. An aqueous waste stream 60 is removed from decanter/coalesce 58 and removed from the process. Organic stream 61 can then be dried within drier 64, which may include, for example, molecular sieves. An optional feed of nitrogen 66 may be introduced to drier 64. Volatiles exiting drier 64 can be routed to an incinerator 68.

Stream 69, which contains the desired 1,1,1,2,3-pentachloropropane product, can be further fractionated to isolate the desired 1,1,1,2,3-pentachloropropane using techniques as described above. For example, stream 69, which can optionally be dried stream 69, can be routed to a distillation column 24 for further fractionating. Advantageously, stream 69 is substantially free of ferric chloride or other catalytic materials that could promote dehydrochlorination of the 1,1,1,2,3-pentachloropropane, and therefore efficient fractionating of stream 69 may be performed. The term "substantially free of ferric chloride" refers to that amount of ferric chloride or less that will not have an appreciable impact on the ability to further fractionate the 1,1,1,2,3-pentachloropropane from other constituents within dried organic stream 69. In particular embodiments, dried organic stream 69 includes less than 10 ppm, in other embodiments less than 5 ppm, and in other embodiments less than 1 ppm by weight ferric chloride.

In one or more embodiments, column 24 can be operated at or under pressures greater than 0.040 atmospheres, in other embodiments greater than 0.050 atmospheres, in other embodiments greater than 0.070 atmospheres, in other embodiments greater than 0.095 atmospheres, and in other embodiments greater than 0.105 atmospheres. In these or other embodiments, column 24 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, distillation column 24 is operated at from about 0.050 to about 0.250 atmospheres or in other embodiments from about 0.095 to about 0.130 atmospheres.

As shown in FIG. 3, the volatiles fraction 25 from distillation column 24 may include a first fraction 26, which may also be referred to as side draw 26, that includes 1,1,1,3-tetrachloropropane and 1,1,3-trichloropropene, and a second fraction 29 that includes light ends, which include those compounds that are more volatile than the 1,1,1,3-tetrachloropropane and 1,1,3-trichloropropene. In one or more embodiments, first fraction 26 may be recycled back to one or more processes. For example, first fraction 26 can be recycled back to a reactor in which crude 12 is produced.

The bottoms fraction 28 from distillation column 24, which contains the desired 1,1,1,2,3-pentachloropropane product, may be further fractioned to isolate the 1,1,1,2,3-pentachloropropane from other high boiling compounds within bottom fraction 28. For example, bottoms fraction 28 may be routed to a second distillation column 30.

In one or more embodiments, second distillation column 30 is operated at pressures greater than 0.040 atmospheres, in other embodiments greater than 0.050 atmospheres, in other embodiments greater than 0.070 atmospheres, in other embodiments greater than 0.095 atmospheres, and in other embodiments greater than 0.105 atmospheres. In these or other embodiments, second distillation column 30 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, second distillation column 30 is operated at from about 0.050 to about 0.250 atmospheres or in other embodiments from about 0.095 to about 0.130 atmospheres. The desired 1,1,1,2,3-pentachloropropane product 45 is collected as a separate stream from heavy ends 46 leaving second distillation column 30.

Fourth Embodiment—Distillation with Incomplete Reaction

In yet another embodiment, the present invention provides a process whereby purified 1,1,1,2,3-pentachloropropane is isolated and purified 1,1,2,3-tetrachloropropene is produced and isolated from a crude product stream containing 1,1,1,2,3-pentachloropropane. These embodiments take advantage of the discovery that by adjusting the temperature and pressure within a reactive distillation column, 1,1,1,2,3-pentachloropropane contained within the crude can be separated from the ferric chloride while simultaneously converting some of the 1,1,1,2,3-pentachloropropane to 1,1,2,3-tetrachloropropene. Additionally, the level of ferric chloride present within the crude product stream containing 1,1,1,2,3-pentachloroprane can, either alone or in combination with temperature and pressure, provide the ability to convert some of the 1,1,1,2,3-pentachloropropane to 1,1,2,3-tetrachloropropene while some 1,1,1,2,3-pentachloropropane can be isolated. Advantageously, both the 1,1,1,2,3-pentachloropropane and the 1,1,2,3-tetrachloropropene, as well as other volatile by-products, can be separated from the ferric chloride and other solid materials within the crude. Further downstream fractionating of the volatiles fraction that leaves the reactive distillation can then be used to isolate the 1,1,1,2,3-pentachloropropane and 1,1,2,3-tetrachloropropene, respectively.

In one or more embodiments, reactive distillation of the crude 1,1,1,2,3-pentachloropropane stream takes place at temperatures of at least 90° C., in other embodiments at least 100° C., and in other embodiments at least 110° C. In these or other embodiments, reactive distillation of the crude 1,1,1,2,3-pentachloropropane stream takes place at temperatures of at most 150° C., in other embodiments at most 140° C., and in other embodiments at most 130° C. In particular embodiments, reactive distillation of the crude 1,1,1,2,3-pentachloropropane stream takes place at a temperature from about 100 to about 140° C., or in other embodiments from about 110 to about 130° C.

In one or more embodiments, reactive distillation of the crude 1,1,1,2,3-pentachloropropane stream takes place at pressures greater than 0.040 atmospheres, in other embodiments greater than 0.050 atmospheres, and in other embodiments greater than 0.060 atmospheres. In these or other embodiments, reactive distillation of the crude 1,1,1,2,3-pentachloropropane stream takes place at pressures less than 0.35 atmospheres, in other embodiments less than 0.25 atmospheres, and in other embodiments less than 0.15 atmospheres. In particular embodiments, reactive distillation of the crude 1,1,1,2,3-pentachloropropane stream takes place at pressures from about 0.040 to about 0.35 atmospheres, or in other embodiments from about 0.050 to about 0.25 atmospheres.

In one or more embodiments, reactive distillation of the crude 1,1,1,2,3-pentachloropropane stream takes place in the presence of at least 100 ppm, in other embodiments at least 500 ppm, in other embodiments at least 1,000 ppm, and in other embodiments at least 2,000 ppm by weight ferric chloride. In particular embodiments, the reactive distillation of the crude 1,1,1,2,3-pentachloropropane stream takes place in the presence of from about 100 to about 5,000 ppm, in other embodiments from about 1,000 to about 4,000 ppm, and in other embodiments from about 1,500 to about 3,000 ppm by weight ferric chloride. As described above, the crude product stream containing the 1,1,1,2,3-pentachloropropane may generally include from about 50 to about 500 ppm by weight ferric chloride. Accordingly, practice of these embodiments may include the step of adding additional ferric chloride to the crude product stream prior to reactive distillation. In one or more embodiments, at least 1 ppm, in other embodiments at least 100 ppm, in other embodiments at least 500 ppm, and in other embodiments at least 1,000 ppm by weight ferric chloride is added to the crude product stream. In particular embodiments, from about 1 to about 3,000 ppm, in other embodiments from about 10 to about 2,500 ppm, and in other embodiments from about 1,000 to about 2,000 ppm by weight ferric chloride is added to the crude product stream.

Figure 4:
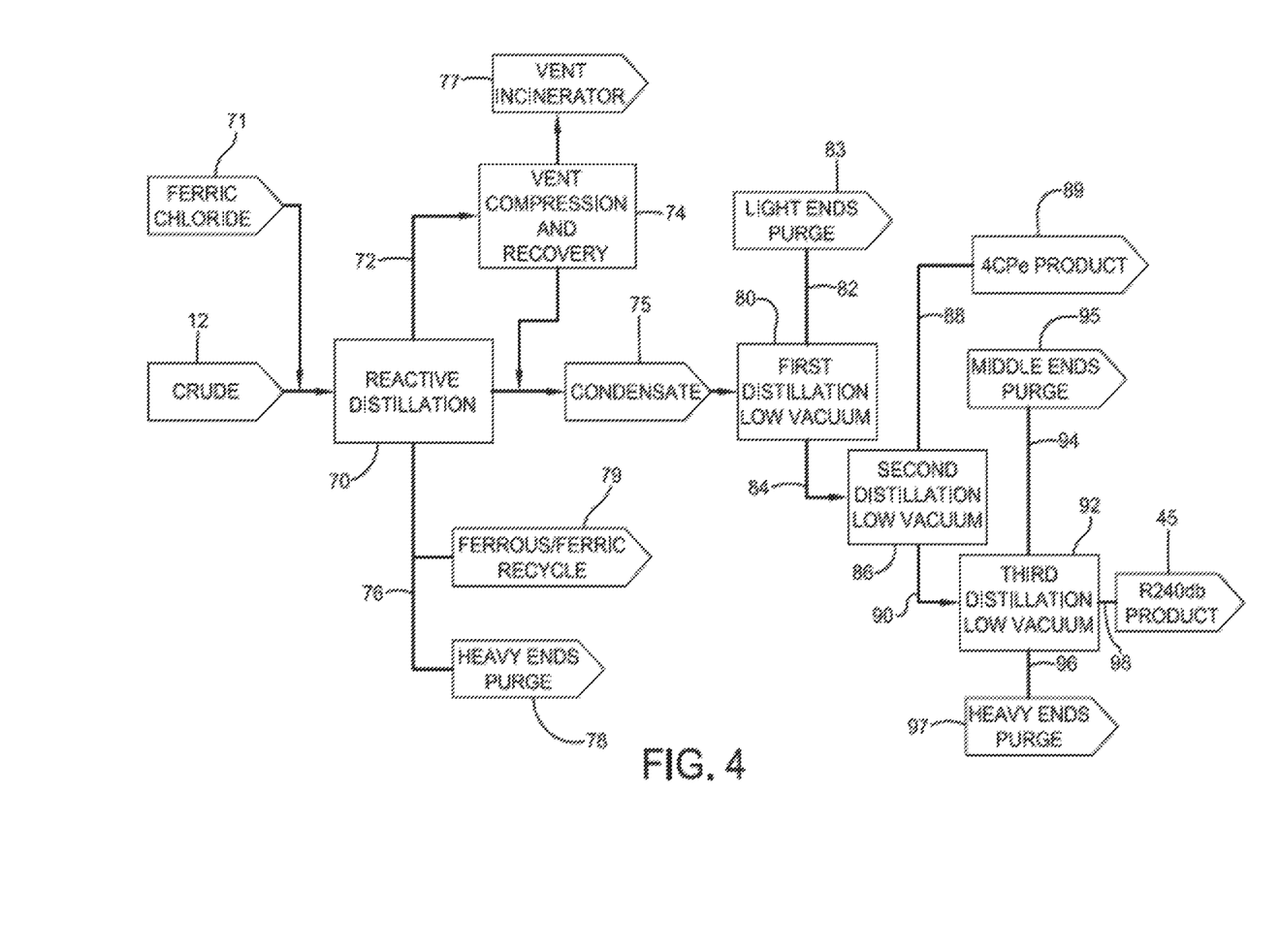
FIG. 4 is a schematic representation of a process for isolating 1,1,1,2,3-pentachloropropane according to one or more embodiments of the invention where 1,1,2,3-tetrachloropropene is simultaneously produced.

An exemplary process for partially converting 1,1,1,2,3-pentachloropropane to 1,1,2,3-tetrachloropropene and isolating the same is shown in FIG. 4. The process includes providing a crude product stream 12, which includes 1,1,1,2,3-pentachloropropane, and delivering the same to a reactive distillation column 70, wherein crude 12 is distilled under appropriate heat and pressure to form condensate fraction 75 that includes both 1,1,1,2,3-pentachloropropane and 1,1,2,3-tetrachloropropene at desired levels, as well as other volatile by-products. As suggested above, this reactive distillation may take place at temperatures from about 100 to about 140° C. and pressures from about 0.040 to about 0.35 atmospheres. As also suggested above, ferric chloride 71 can be added to the crude product stream 12. In one or more embodiments, ferric chloride 71 can be added before crude product stream 12 is introduced to reactive distillation column 70. In other embodiments, ferric chloride 71 can be introduced to crude product stream 12 within reactive distillation column 70.

A volatiles fraction 72 may be collected from column 70 and is then condensed. Volatiles fraction 72 can be routed to a compression and recovery unit 74 where the volatiles fraction 72 can be at least partially condensed and combined with condensate 75. Volatiles exiting compression and recovery unit 74 may be routed to an incinerator 77.

The bottom fraction 76 from reactive distillation column 70 can be routed to heavy ends purge 78. In one or more embodiments, a portion of bottom fraction 76, especially the fraction believed to contain iron chlorides, can be recycled back to one or more processes where ferric chloride is employed. For example, iron chlorides 79 can be recycled back to a reactor in which crude 12 is produced.

In one or more embodiments, condensate 75 can be further fractioned to isolate the 1,1,1,2,3-pentachloropropane and 1,1,2,3-tetrachloropropene from other compounds that were distilled from reactive distillation column 70. For example, condensate 75 is routed to a distillation column 80 for further fractioning. Advantageously, condensate 75 is substantially free of ferric chloride or other catalytic materials that can promote dehydrochlorination of the 1,1,1,2,3-pentachloropropane.

In one or more embodiments, distillation column 80 can be operated at or under pressures greater than 0.050 atmospheres, in other embodiments greater than 0.070 atmospheres, in other embodiments greater than 0.095 atmospheres, and in other embodiments greater than 0.105 atmospheres. In these or other embodiments, column 80 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, distillation column 24 is operated at from about 0.050 to about 0.250 atmospheres or in other embodiments from about 0.095 to about 0.130 atmospheres.

As shown in FIG. 4, volatiles fraction 82 from distillation column 80 may include those compounds more volatile than 1,1,1,2,3-pentachloropropane and 1,1,2,3-tetrachloropropene, and these compounds may be removed from the process as light ends purge 83.

The bottoms fraction 84 from distillation column 80, which includes both 1,1,1,2,3-pentachloropropane and 1,1,2,3-tetrachloropropene, may be further fractioned to isolate the 1,1,2,3-tetrachloropropene product, which is more volatile than the 1,1,1,2,3-pentachloropropane. For example, bottoms fraction 84 may be routed to a second distillation column 86.

In one or more embodiments, second distillation column 86 can be operated at pressures greater than 0.050 atmospheres, in other embodiments greater than 0.070 atmospheres, in other embodiments greater than 0.095 atmospheres, and in other embodiments greater than 0.105 atmospheres. In these or other embodiments, distillation column 86 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, second distillation column 86 is operated at from about 0.050 to about 0.250 atmospheres or in other embodiments from about 0.095 to about 0.130 atmospheres.

In one or more embodiments, second distillation column 86 is operated at conditions to isolate 1,1,2,3-tetrachloropropene in a volatiles fraction 88 where 1,1,2,3-tetrachloropropene product 89 can be isolated and collected. Bottoms fraction 90 from second distillation column 86, which contains 1,1,1,2,3-pentachloropropane product, may be further fractioned to isolate the 1,1,1,2,3-pentachloropropane from other compounds within bottoms fraction 90. For example, bottoms fraction 90 may be routed to a third distillation column 92.

In one or more embodiments, third distillation column 92 can be operated at pressures greater than 0.050 atmospheres, in other embodiments greater than 0.070 atmospheres, in other embodiments greater than 0.095 atmospheres, and in other embodiments greater than 0.105 atmospheres. In these or other embodiments, third distillation column 92 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, third distillation column 86 can be operated at from about 0.050 to about 0.250 atmospheres or in other embodiments from about 0.095 to about 0.130 atmospheres.

Compounds having a lower boiling point than 1,1,1,2,3-pentachloropropane may form a volatiles fraction 94 and be removed from third distillation column 92 as middle ends purge 95. An example of a compound having a lower boiling point than 1,1,1,2,3-pentachloropropane that is likely to be removed as middle ends purge 95 is pentachloropropene. The bottoms fraction 96 from third distillation column 92 is removed as heavy ends purge 97. The desired 1,1,1,2,3-pentachloropropane product 45 is removed from third distillation column 92 as stream 98.

Fifth Embodiment—Side Draw

In still another embodiment, 1,1,1,2,3-pentachloropropane is isolated from a crude product stream including the 1,1,1,2,3-pentachloropropane by using a side draw tray positioned near the bottom of a packed column wherein reactive distillation of the crude 1,1,1,2,3-pentachloropropane stream is reactively distilled. This process takes advantage of the fact that 1,1,1,2,3-pentachloropropane has a lower vapor pressure (i.e., higher boiling point) than the 1,1,2,3-tetrachloropropene, the latter of which is produced by dehydrochlorination within the reactive distillation column. Thus, the reactive distillation column includes a gradient of 1,1,1,2,3-petachloropropane within the bottom of the column and part way up the height of the column, with the greatest concentration of 1,1,1,2,3-pentachloroproane existing in the bottom of the column. The side-draw tray is positioned at a location near the top of this gradient. In one or more embodiments, sufficient packing material is provided at or near the draw tray to inhibit iron chlorides from entering the 1,1,1,2,3-pentachloropropane stream exiting the column via the side draw. In one or more embodiments, the gradient is defined by column packing. As the skilled person understands, this column packing may include structured packing materials such as metal structured packing materials. In other embodiments, the gradient is defined by the column design.

Figure 5:
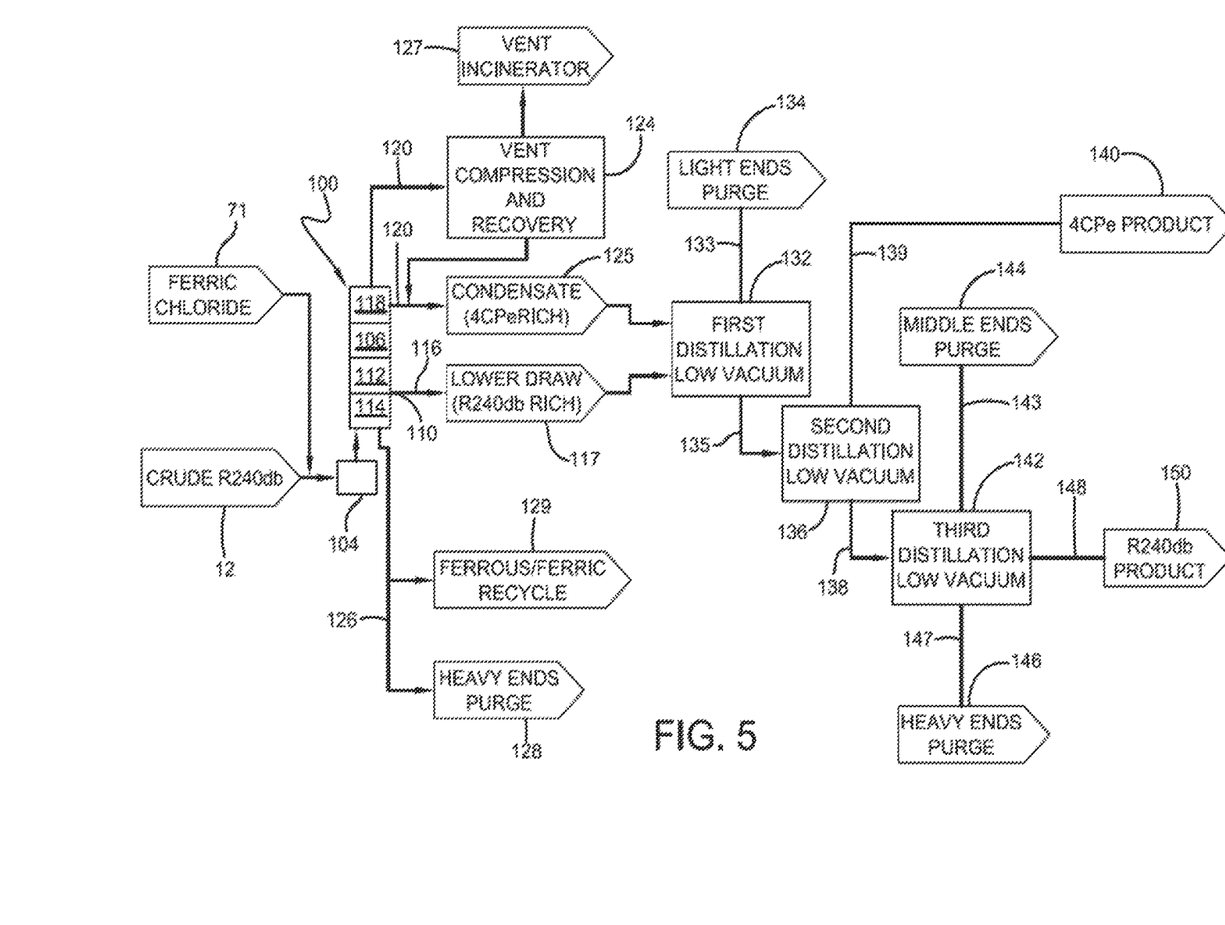
FIG. 5 is a schematic representation of a process for isolating 1,1,1,2,3-pentachloropropane according to one or more embodiments of the invention where a side draw tray is used in a reactive distillation column.

An example of this embodiment is shown in FIG. 5. In one or more embodiments, crude 1,1,1,2,3-pentachloropropane stream 12 enters reactive distillation column 100 via a recycle loop 104. As with the previous embodiments, ferric chloride 71 can be added to stream 12. Column 100 is operated under conditions of temperature and pressure sufficient to dehydrochlorinate 1,1,1,2,3-pentachloropropane to 1,1,2,3-tetrachloropropene.

In one or more embodiments, reactive distillation column 100 is operated at a temperature of at least 60° C., in other embodiments at least 100° C., and in other embodiments at least 150° C. In these or other embodiments, reactive distillation column 100 is operated at temperatures of at most 200° C., in other embodiments at most 150° C., and in other embodiments at most 100° C.

As shown in FIG. 5, column 100 includes column packing 106, and a side draw tray 110 at or near the bottom 112 of column packing 106. It is believed that 1,1,1,2,3-pentachloropropane concentrates within column 100 and is captured by tray 110 before returning to the bottom chamber 114 of column 100. The condensed material 117 captured at tray 110 is believed to include concentrated 1,1,1,2,3-pentachloropropane and is removed from column 100 via side draw stream 116, which may also be referred to as lower draw 116. In one or more embodiments, stream 116 may advantageously be substantially free of ferric chloride or other catalytic materials that could promote dehydrochlorination of the 1,1,1,2,3-pentachloropropane, and therefore efficient fractionating of stream 116 may be performed. The term "substantially free of ferric chloride" refers to that amount of ferric chloride or less that will not have an appreciable impact on the ability to further fraction the 1,1,1,2,3-pentachloropropane from other constituents within stream 116. In particular embodiments, stream 116 includes less than 100 ppm, in other embodiments less than 10 ppm, in other embodiments less than 5 ppm, and in other embodiments less than 1 ppm by weight ferric chloride.

Exiting column 100 at the top 118 is volatiles stream 120, which includes 1,1,2,3-tetrachloropropene. Volatiles fraction 120 may be condensed and collected from column 100 as a condensate stream 125 (which is rich in 1,1,2,3-tetrachloropropene) or volatiles fraction 120 can be routed to a compression and recovery unit 124 where the volatiles fraction 120 can be at least partially condensed and combined with condensate stream 125. Volatiles exiting compression and recovery unit 124 may be routed to an incinerator 127.

The bottom fraction 126 from reactive distillation column 100 can be routed to heavy ends purge 128. In one or more embodiments, a portion of bottom fraction 126, especially the fraction believed to contain iron chlorides, can be recycled back to one or more processes where ferric chloride is employed. For example, iron chlorides 129 can be recycled back to a reactor in which crude 12 is produced.

Accordingly, the process of this embodiment produces two enriched streams; the first stream (e.g., stream 116) includes concentrated 1,1,1,2,3-pentachloropropane and the second stream (e.g., stream 125) includes concentrated 1,1,2,3-tetrachloropropene. As with other embodiments, these two streams can be further purified to produce purified streams of 1,1,1,2,3-pentachloropropane and 1,1,2,3-tetrachloropropene, respectively.

For example, in one or more embodiments, lower draw 116 and condensate 125 can be further fractioned to remove compounds that are lighter than 1,1,2,3-tetrachloropropene (and 1,1,1,2,3-pentachloropropane). For example, streams 116 and 125 may be separately and individually routed to a distillation column 132 for further fractioning. Advantageously, a single column, such as column 132, may be used wherein stream 125 (which is rich in 1,1,2,3-tetrachloropropene) is routed to an elevated location in column 132 and stream 116 (which is rich is 1,1,1,2,3-pentachloropropane) is routed to a lower location in column 132.

In one or more embodiments, distillation column 132 can be operated at or under pressures greater than 0.050 atmospheres, in other embodiments greater than 0.070 atmospheres, in other embodiments greater than 0.095 atmospheres, and in other embodiments greater than 0.105 atmospheres. In these or other embodiments, column 132 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, distillation column 132 is operated at from about 0.050 to about 0.250 atmospheres or in other embodiments from about 0.095 to about 0.130 atmospheres.

As shown in FIG. 5, volatiles fraction 133 from distillation column 132 may include those compounds more volatile than 1,1,1,2,3-pentachloropropane and 1,1,2,3-tetrachloropropene, and these compounds may be removed from the process as light ends purge 134.

The bottoms fraction 135 from distillation column 132, which includes both 1,1,1,2,3-pentachloropropane and 1,1,2,3-tetrachloropropene, may be further fractioned to isolate the 1,1,2,3-tetrachloropropene product, which is more volatile than the 1,1,1,2,3-pentachloropropane. For example, bottoms fraction 135 may be routed to a second distillation column 136.

In one or more embodiments, second distillation column 136 can be operated at pressures greater than 0.050 atmospheres, in other embodiments greater than 0.070 atmospheres, in other embodiments greater than 0.095 atmospheres, and in other embodiments greater than 0.105 atmospheres. In these or other embodiments, distillation column 136 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, second distillation column 136 is operated at from about 0.050 to about 0.250 atmospheres or in other embodiments from about 0.095 to about 0.130 atmospheres.

In one or more embodiments, second distillation column 136 is operated at conditions to isolate 1,1,2,3-tetrachloropropene in a volatiles fraction 139 where 1,1,2,3-tetrachloropropene product 140 can be isolated and collected. Bottoms fraction 138 from second distillation column 136, which contains 1,1,1,2,3-pentachloropropane product, may be further fractioned to isolate the 1,1,1,2,3-pentachloropropane from other compounds within bottoms fraction 138. For example, bottoms fraction 138 may be routed to a third distillation column 142.

In one or more embodiments, third distillation column 142 can be operated at pressures greater than 0.050 atmospheres, in other embodiments greater than 0.070 atmospheres, in other embodiments greater than 0.095 atmospheres, and in other embodiments greater than 0.105 atmospheres. In these or other embodiments, third distillation column 142 can be operated at or under pressures less than 0.250 atmospheres, in other embodiments less than 0.170 atmospheres, in other embodiments less than 0.130 atmospheres, and in other embodiments less than 0.110 atmospheres. In particular embodiments, third distillation column 142 can be operated at from about 0.050 to about 0.250 atmospheres or in other embodiments from about 0.095 to about 0.130 atmospheres.

Compounds having a lower boiling point than 1,1,1,2,3-pentachloropropane may form a volatiles fraction 143 and be removed from third distillation column 142 as middle ends purge 144. An example of a compound having a lower boiling point than 1,1,1,2,3-pentachloropropane that is likely to be removed as middle ends purge 144 is pentachloropropene. The bottoms fraction 147 from third distillation column 142 is removed as heavy ends purge 146. The desired 1,1,1,2,3-pentachloropropane product 150 is removed from third distillation column 142 as stream 148.

EXAMPLES

In order to demonstrate the practice of the present invention, the following examples have been prepared and tested. The examples should not, however, be viewed as limiting the scope of the invention. The claims will serve to define the invention.

The sample experiments set forth herein were conducted within a 20-tray, 25 mm i.d. vacuum-jacketed Pyrex laboratory distillation column equipped with a 1-liter bottoms flask and means for operation at sub-atmospheric pressure. A swinging-bucket type reflux head allowed controlled withdrawal of overhead product. The bottoms flask of the distillation column was charged, as batch, with crude 1,1,1,2,3-pentachloropropane, which was prepared in accordance with the teachings of U.S. Pat. No. 8,115,038. The Table I provides amount of crude used in each example together with the relative amounts of some relevant constituents thereof. The column pressure was adjusted to about 0.24–0.27 atmospheres, and sufficient heat was applied to the bottoms flask to reflux liquid in the column (e.g. about 140–150° C.). The distillation was conducted over several hours. The formation rate of 1,1,2,3-tetrachloropropene, as indicated by a measurement within a specified time interval, was evaluated and representative data is reported in the Table I.

TABLE I

| Sample | 1 | 2 | 3 | 4 | 5 |
| --- | --- | --- | --- | --- | --- |
| Inhibitor | N/A | TBP | TBP | Dodecane | Dodecane |
| Inhibitor Amount (ppmw) | N/A | 1532 | 155 | 1078 | 2215 |
| Molar Ratio Inhibitor: Ferric Chloride | N/A | 10:1 | 1:1 | 10:1 | 20:1 |
| Sample Weight (g) | 1118.6 | 1162.2 | 1096.8 | 1011.1 | 943.6 |
| 1,1,1,2,3-pentachloropropane (%) | 77.725 | 77.725 | 77.725 | 78.006 | 77.984 |
| Ferric Chloride (ppm) | 93 | 93 | 93 | 93 | 93 |
| 1,1,2,3-tetrachloropropene (%) | 0.643 | 0.643 | 0.643 | 0.667 | 0.755 |
| Overhead 1,1,2,3-tetrachloropropene | | | | | |
| 1-4 hours reflux (%) | 25.441 | 2.817 | 2.974 | 6.552 | 4.706 |
| 4-6 hours reflux (%) | 12.725 | 1.003 | 0.901 | 3.005 | 1.578 |

As generally indicated by the Table I, in the absence of an inhibitor, 1,1,1,2,3-pentachloropropane was readily converted to 1,1,2,3-tetrachloropropene as a result of the distillation process; i.e. dehydrochlorination took place. When TBP was present, however, even at amounts as low as 1 mole of TBP per mole of ferric chloride, dehydrochlorination to 1,1,2,3-tetrachloropropene was advantageously inhibited. Similar advantageous results were achieved in the presence of dodecane, although analysis shows that greater amounts of dodecane may be desirable to achieve more appreciable inhibition of the dehydrochlorination reaction.

In a second experiment, which generally used the same laboratory equipment used in the first experiment, crude 1,1,1,2,3-pentachloropropane, prepared according to the teachings of U.S. Pat. No. 8,115,038, was subjected to low pressure distillation. Specifically, the targeted pressure was 0.03 atmospheres, although limits of the experimental design initially precluded reaching that target. The particulars of the experiment are provided in Table II. In particular, the distillation was conducted over several hours, and the rate of 1,1,2,3-tetrachloropropene within the overhead product was determined as provided in Table II.

TABLE II

| Sample Analyzed/Reflux Time (h) | Charge (t = 0) | t = 0.88 | t = 3.10 | t = 4.67 | t = 6.65 |
|---|---|---|---|---|---|
| 1,1,1,2,3-pentachloropropane (%) | 1.024 | 0.046 | 8.308 | 0.426 | 0.102 |
| Ferric Chloride (ppm) | 131 | — | — | — | — |
| 1,1,2,3-tetrachloropropene (%) | 78.810 | 4.234 | 87.318 | 99.480 | 99.877 |
| Pressure | N/A | 0.14 | 0.05 | 0.03 | 0.03 |

As generally shown in Table II, distillation at low temperatures inhibited conversion of the 1,1,1,2,3-pentachloropropane to 1,1,2,3-tetrachloropropene; i.e., dehydrochlorination was inhibited.

Various modifications and alterations that do not depart from the scope and spirit of this invention will become apparent to those skilled in the art. This invention is not to be duly limited to the illustrative embodiments set forth herein.

What is claimed is:

1. A process for isolating 1,1,1,2,3-pentachloropropane from a crude product stream containing the 1,1,1,2,3-pentachloropropane, the process comprising:
   (a.) providing a crude product stream containing 1,1,1,2,3-pentachloropropane, where the crude product stream further includes ferric chloride;
   (b.) adding an inhibitor to the crude product stream to deactivate the ferric chloride, wherein the inhibitor is tributylphosphate, and wherein the amount of inhibitor added to the crude product stream is from about 0.5 moles to about 2.0 moles of inhibitor per mole of ferric chloride within the crude product stream.

2. The process of claim 1, wherein the amount of inhibitor added to the crude product stream is from about 0.7 moles to about 1.3 moles of inhibitor per mole of ferric chloride within the crude product stream.

3. The process of claim 1, wherein the crude product stream includes at least 50 ppm ferric chloride.

4. The process of claim 1, wherein, following step (b), the crude product stream remains relatively clear with no appreciable amount of solids.

5. The process of claim 1, further comprising the steps of
   (c.) after said step of adding an inhibitor, subjecting the crude product stream to distillation to thereby form a 1,1,1,2,3-pentachloropropane stream that is substantially free of ferric chloride; and
   (d.) further processing the 1,1,1,2,3-pentachloropropane stream to isolate the 1,1,1,2,3-pentachloropropane.

6. The process of claim 5, wherein the 1,1,1,2,3-pentachloropropane stream includes less than 10 ppm ferric chloride.

7. The process of claim 5, wherein said step of subjecting the crude product stream to distillation takes place at pressures less than 0.040 atmospheres.

8. A process for isolating 1,1,1,2,3-pentachloropropane from a crude product stream containing the 1,1,1,2,3-pentachloropropane, the process comprising:
   (a.) providing a crude product stream containing 1,1,1,2,3-pentachloropropane, where the crude product stream further includes at least 50 ppm ferric chloride;
   (b.) adding from about 0.5 moles to about 2 moles of tributylphosphate, per mole of ferric chloride within the crude product stream, to the crude product stream, wherein said step of adding deactivates the ferric chloride in the crude product stream.

9. The process of claim 8, wherein the amount of tributylphosphate added to the crude product stream is from about 0.7 to about 1.3 moles of tributylphosphate per mole of ferric chloride within the crude product stream.

10. The process of claim 8, wherein, following step (b), the crude product stream remains relatively clear with no appreciable amount of solids.

11. A crude product composition comprising 1,1,1,2,3-pentachloropropane, at least 50 ppm ferric chloride, and from about 0.5 moles to about 2 moles of tributylphosphate, per mole of ferric chloride.

12. The composition of claim 11, wherein the amount of tributylphosphate is from about 0.7 to about 1.3 moles of tributylphosphate per mole of ferric chloride.

13. The composition of claim 11, further comprising about 5 to about 30 wt. % carbon tetrachloride.

14. The composition of claim 11, comprising from about 70 to about 200 ppm by weight ferric chloride.

15. The composition of claim 11, wherein the composition occurs following a residence tank wherein residual chlorine has been converted to the 1,1,1,2,3-pentachloropropane.

16. The composition of claim 11, wherein, following a predetermined reaction time, the composition remains relatively clear with no appreciable amount of solids.

* * * * *